United States Patent
Weisman et al.

(10) Patent No.: US 7,169,768 B1
(45) Date of Patent: *Jan. 30, 2007

(54) METHOD OF DECREASING ATHEROSCLEROSIS AND ITS COMPLICATIONS

(76) Inventors: Kenneth M. Weisman, 30 Springton Pointe Dr., Newtown Square, PA (US) 19073; Michael Goldberg, 20 Aspen Dr., Ivyland, PA (US) 18974

( * ) Notice: Subject to any disclaimer, the term of this patent is extended or adjusted under 35 U.S.C. 154(b) by 0 days.

This patent is subject to a terminal disclaimer.

(21) Appl. No.: 09/089,583

(22) Filed: Jun. 3, 1998

Related U.S. Application Data

(60) Provisional application No. 60/049,746, filed on Jun. 12, 1998, provisional application No. 60/049,003, filed on Jun. 9, 1997, provisional application No. 60/049,160, filed on Jun. 9, 1997, provisional application No. 60/049,162, filed on Jun. 9, 1997, provisional application No. 60/049,169, filed on Jun. 9, 1997, provisional application No. 60/041,070, filed on Mar. 18, 1997.

(51) Int. Cl.
*A61K 31/56* (2006.01)
*A61K 31/535* (2006.01)
*A61K 31/34* (2006.01)

(52) U.S. Cl. .................. 514/177; 514/178; 514/236.2; 514/310; 514/324; 514/428; 514/448; 514/470; 514/565

(58) Field of Classification Search ................ 514/177, 514/178, 236.2, 310, 470, 565, 324, 448, 514/428
See application file for complete search history.

(56) References Cited

U.S. PATENT DOCUMENTS

| 5,770,609 | A | * | 6/1998 | Grainger et al. | 514/319 |
| 5,872,114 | A | * | 2/1999 | Labrie | 514/178 |
| 5,906,987 | A | * | 5/1999 | Chwalisz et al. | 514/177 |
| 6,099,851 | A | * | 8/2000 | Weisman et al. | 424/423 |
| 6,140,315 | A | * | 10/2000 | Weisman et al. | 514/177 |
| 6,197,337 | B1 | * | 3/2001 | Weisman et al. | 424/422 |

FOREIGN PATENT DOCUMENTS

WO 9608239 * 3/1996

OTHER PUBLICATIONS

Goodman and Gilman's Pharmacological Basis of Therapeutics, pp. 1427-1429, 1980.*

* cited by examiner

*Primary Examiner*—James O. Wilson
*Assistant Examiner*—Howard V. Owens, Jr.
(74) *Attorney, Agent, or Firm*—Caesar, Rivise, Bernstein, Cohen & Pokotilow, Ltd.

(57) ABSTRACT

A method of decreasing atherosclerosis and its complications including but not limited to myocardial infarction, stroke and peripheral vascular disease wherein the method involves administering to a human or an animal an amount of an inhibitor of the release of LHRH or GnRH.

1 Claim, No Drawings

METHOD OF DECREASING ATHEROSCLEROSIS AND ITS COMPLICATIONS

CROSS-REFERENCES TO RELATED APPLICATIONS

This application claims the benefit of the filing dates of Provisional Patent Applications Ser. Nos. 60/049,003 (filing date Jun. 9, 1997); 60/049,160 (filing date Jun. 9, 1997); 60/049,746 (filing date Jun. 12, 1998); 60/049,162 (filing date Jun. 9, 1997); 60/049,169 (filing date Jun. 9, 1997); 60/041,070 (filing date Mar. 18, 1997).

There are no rights to inventions made under federally-sponsored research and development. The present invention was made entirely using private funds.

BACKGROUND OF THE INVENTION

1. Field of the Invention

There are many steps in the biosynthesis and utilization by the tissues of testosterone. Testosterone is made mostly in the testicles. A lesser amount is made in the adrenals. Production is stimulated by secretion of Gn RH or LHRH by the brain, which causes secretion of luteinizing hormone (LH) by the pituitary, which causes the testicles to make testosterone. Testosterone then flows into the blood stream and is absorbed by the target cells. Here it binds to a receptor and is transported into the cell and converted to dihydrotestosterone. This is bound and carried to the nucleus of the cell where it redirects cellular activity by turning on and off DNA. Hormonal manipulation is a term which refers to the reduction of testosterone or its effects by blocking any step in the above process in order to gain a desired effect. Until now the uses of hormonal manipulation include for example treating prostatic carcinoma, and treatment for baldness.

2. Description of Related Prior Art

The present invention involves the use of hormonal manipulations in the prevention and treatment of atherosclerosis, coronary heart disease, stroke and peripheral vascular disease.

Leuprolide acetate is a synthetic nonapeptide of naturally occurring gonadotropin-releasing hormone (GnRH or LH—RH), the chemical name is 5-oxo-L-prolyl-L-histidyl-L-tryptophyl-L-seryl-L-tyrosyl-D-leucyl-L-leucyl-L-arginyl-N-ethyl-L-prolinamide acetate salt sold under the trade name Lupron or Lupron Depot, as identified by U.S. Pat. No. 4,897,256, the entire disclosure is incorporated by reference herein, is known for use in the treatment of prostatic carcinoma. Leuprolide is a potent inhibitor of gonadotropin secretion known to decrease levels of LHRH, LH and Testosterone.

Goserelin Acetate, a synthetic decapeptide analogue of LHRH or GnRH, is chemically described as an acetate salt of [D-Ser(Bu$^t$)$^6$Azgly$^{10}$]LHRH. Its chemical structure is pyro-Glu-His-Trp-Ser-Tyr-D-Ser(Bu)-Leu-Arg-Pro-Azgly-NH2 acetate [C59H84N18O14 (C2H4O2) sold under the trade name Zoladex, as identified by the U.S. Pat. No. 5,510,460, the entire disclosure is incorporated by reference herein, is known for the use in treatment of prostatic carcinoma. Goserelin acetate is a potent inhibitor of gonadotropin secretion known to reduce levels of GnRH or LHRH, LH and Testosterone.

Nilutamide, a nonsteroidal, orally active, antiandrogen, having the chemical name 5,5-dimethyl 3-[4-nitro-3-(trifluoromethyl)phenyl]2,3-imidazolidinedione, sold under the trade name Nilandron, as identified by U.S. Pat. No. 5,023, 088, the entire disclosure is incorporated by reference herein, is known for use in treatment of prostatic carcinoma.

Flutamide, an acetanilid, nonsteroidol androgen having the chemical name, 2-methyl-N-[4-nitro-3-(trifluoromethyl) phenyl]propanamide sold under the trade name Eulexin, as identified by U.S. Pat. Nos. 3,995,060 and 4,474,813, the entire disclosure of which are incorporated by reference herein, Flutamide is known for use in treatment of prostatic carcinoma.

Bicalutamide, a non-steroidal antiandrogen, chemical name is propanamide, N-(4cyano-3-(trifluoromethyl)phenyl]-3-[(4-fluorophenyl)sulfonyl]-2-hydroxy-2-methyl-(+−) sold under the trade name Casodex, as identified by U.S. Pat. No. 4,636,505, the entire disclosure is incorporated by reference herein, is known for use in treatment of prostatic carcinoma.

SUMMARY OF THE INVENTION AND DESCRIPTION OF PREFERRED EMBODIMENT

A retrospective study was performed which compared the rates of patient reported heart attack in several groups: 1—control group of males entering the urology office for any routine complaint. 2—a group of prostate cancer patients treated with Leuprolide acetate, a LHRH inhibitor. 3—a group of prostate cancer patients treated with Goserelin acetate (Zoladex), a LHRH inhibitor. 4—a group of prostate cancer patients not treated with hormonal manipulation (neither Leuprolide or Goserelin). 5—a group of patients treated with Finasteride (another form of hormonal manipulation). 6—all patients on LHRH inhibitors (group 2+group 3).

The patients on either leuprolide acetate or goserelin acetate were treated with the recommended doses indicated for the treatment of prostatic carcinoma, at either one or three month intervals depending on the preparation used. Leuprolide was dosed at 7.5 mg monthly (single intramuscular injection) or at 22.5 mg at 3 month intervals (single intramuscular injection). Goserelin was dosed at 3.6 mg monthly (subcutaneous injection) or at a dose of 10.8 mg at 3 month intervals (subcutaneous injection).

The various groups of office patients were given a questionnaire. In groups 2, 3 and 5 only those on drug for at least one year were considered. Cardiac event is defined as either the history of a heart attack or occurrence of coronary artery bypass or angioplasty. In control groups only events occurring in the 3 years prior to the questionnaire are charted. The results were as follows:

|  | No Patients | Cardiac Events | Subject Years | Events/Year |
|---|---|---|---|---|
| Group 1 (control no cancer) | 247 | 26 | 741 | .0351 |
| Group 4 (control cancer patients) | 69 | 6 | 207 | .0290 |
| Total Control (Groups 1 + 4) | 316 | 32 | 948 | .0338 |
| Group 2 leuprolide acetate | 28 | 1 | 118 | .00847 |
| Group 3 goserelin acetate | 25 | 1 | 62 | .0161 |
| Group 5 - (Finasteride) | 91 | 4 | 242 | .0165 |
| Group 6 (antiLHRH) groups 2 + 3 | 50 | 2 | 180 | .0111 |

The observed difference between the proportions of Total Control vs Group 6 (LHRH) is 0.0226. 95% Confidence Interval for the difference between the proportions is 0.00350 to 0.0418. Patients treated with LHRH inhibitors had fewer heart attacks than controls.

The observed difference between the proportions of Group 2 (Lupron) and Total Control is 0.0253. 95% Confidence Interval for the difference between the proportions is 0.00514 and 0.0454. Patients treated with Leuprolide acetate had fewer heart attacks than controls.

The observed difference between the proportions of Group 3 and Total Control is 0.0177. Patients treated with Goserelin (Zoladex) had fewer heart attacks than controls.

The observed difference between the proportions of Group 1 (Control) and Group 5 (Finasteride) is 0.0186. 90% Confidence Interval for the difference between the proportions is 0.00103 to 0.0361. Patients treated with Finasteride had fewer heart attacks than control.

Without further elaboration the foregoing will so fully illustrate our invention that others may, by applying current and future knowledge, adopt the same for use under various conditions of service.

What is claimed is:

1. A method of decreasing atherosclerosis comprising administering to a human or an animal in need thereof an amount of a substance selected from the group consisting of leuprolide acetate, goserelin acetate, flutamide, bicalutamide, and nilutamide, which is an inhibitor of the release of LHRH or GnRH resulting in decreased levels of LH.

* * * * *